United States Patent
Diederich et al.

(10) Patent No.: US 6,746,465 B2
(45) Date of Patent: Jun. 8, 2004

(54) CATHETER BASED BALLOON FOR THERAPY MODIFICATION AND POSITIONING OF TISSUE

(75) Inventors: Chris J. Diederich, Novato, CA (US); Dana L. Deardorff, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 64 days.

(21) Appl. No.: 10/020,583

(22) Filed: Dec. 14, 2001

(65) Prior Publication Data

US 2003/0114878 A1 Jun. 19, 2003

(51) Int. Cl.[7] .............................................. A61M 29/00
(52) U.S. Cl. .................................. 606/192; 604/101.02
(58) Field of Search ................................ 606/191, 192, 606/193, 194, 197, 199; 604/96.01, 97.01, 97.03, 99.01, 100.01

(56) References Cited

U.S. PATENT DOCUMENTS 5,865,801 A * 2/1999 Houser .................... 604/96.01
5,902,308 A * 5/1999 Murphy ...................... 606/191
6,179,858 B1 * 1/2001 Squire et al. ............... 606/198

* cited by examiner

Primary Examiner—Kevin T. Truong
(74) Attorney, Agent, or Firm—John P. O'Banion

(57) ABSTRACT

An apparatus and method for shielding non-target tissues and organs during thermotherapy, brachytherapy or other treatment of a diseased target tissue. The apparatus includes a catheter shaft having input and output lumens and at least one inflatable balloon. A plurality of input lumens within the catheter shaft allows the passage of liquid or gas through an input port and into the interior of the balloon thereby inflating the balloon. The gas or liquid can then be cycled through the inflated balloon through an output port and output lumen and out of the catheter shaft. Temperature sensors or other sensors may be attached to the balloon or catheter to monitor temperature or other conditions at the treatment site. The catheter is positioned between the target tissue or organ and sensitive non-target tissues in proximity to the target tissue and inflated causing a physical separation of tissues as well as a physical shield.

57 Claims, 7 Drawing Sheets

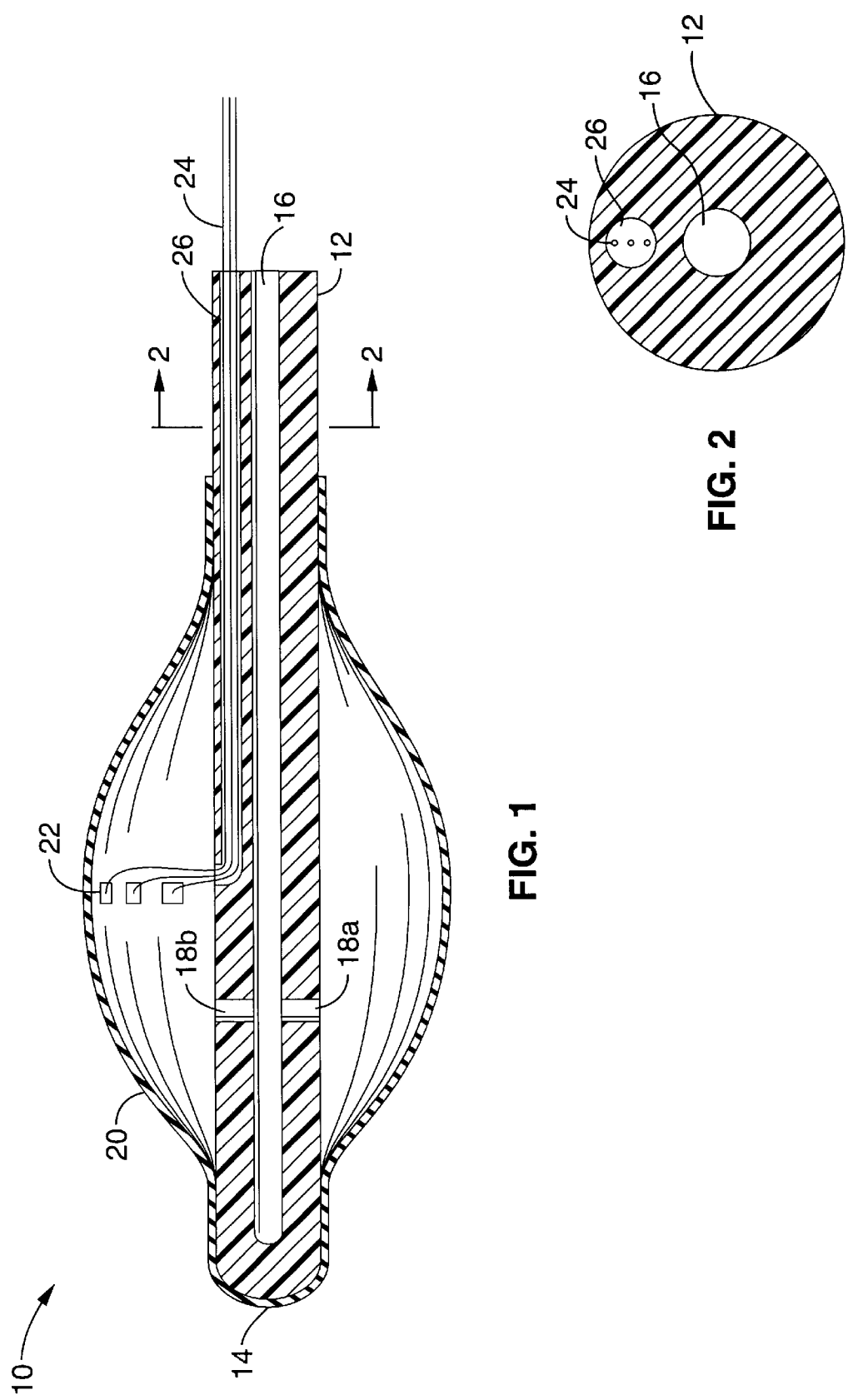

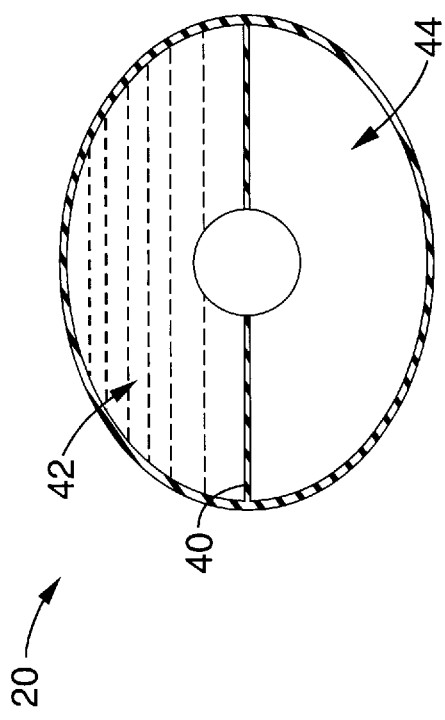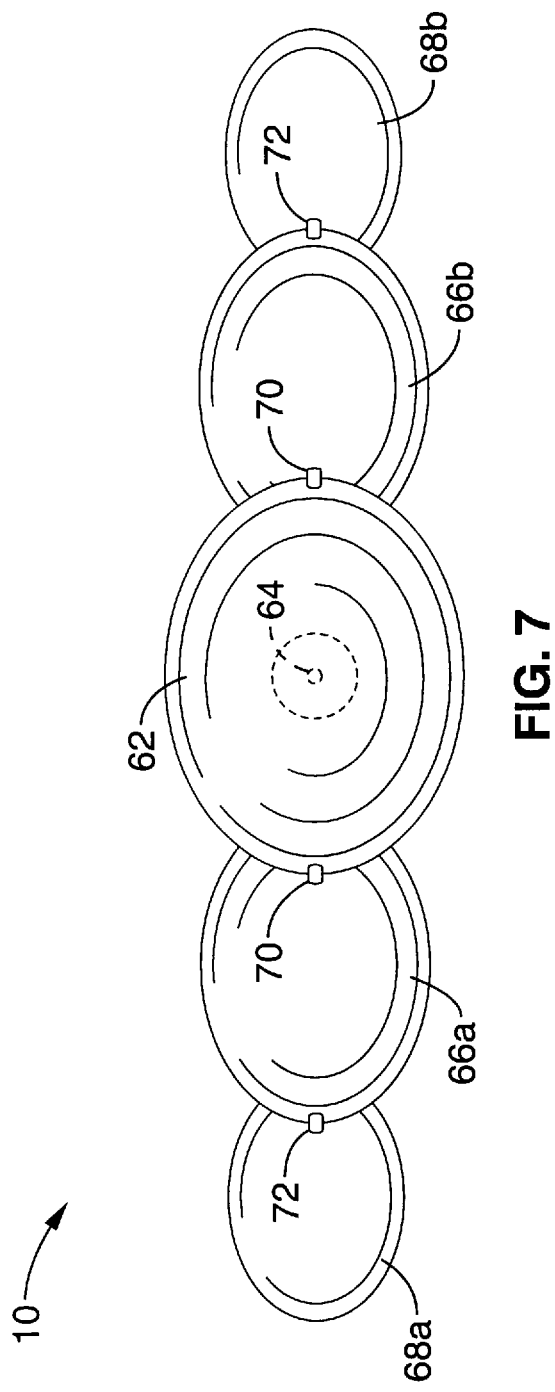

CATHETER BASED BALLOON FOR THERAPY MODIFICATION AND POSITIONING OF TISSUE

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A COMPUTER PROGRAM APPENDIX

Not Applicable

BACKGROUND OF THE INVENTION

1. Field of the Invention

This invention pertains generally to devices that assist with internal diagnostic imaging and treatment procedures, and more particularly to a catheter based balloon for temperature, acoustical and radiological blocking as well as the repositioning of treated and sensitive tissues.

2. Description of the Background Art

Conventional hyperthermia or tissue heating at moderate temperatures (41° C. to 45° C.) has been shown to promote changes in cellular dynamics, tumor microcirculation, and blood vessel permeability that can be exploited to enhance other therapies such as radiation and chemotherapy for cancer treatment, drug delivery and potentiation, gene therapy, and even organ preservation.

The immediate physiological effects of thermal exposure during thermal therapies include heat-induced acceleration of metabolism, thermal inactivation of enzymes, and the rupture of cell membranes. Delayed effects of thermal exposure include intracellular and tissue edema, hyperemia with increasing blood flow, as well as an increase in blood vessel permeability and dilatation.

The damage due to thermal effects alone is reversible for thermal exposures at lower temperatures with relatively shorter times of exposure (non-lethal thermal doses). For exposures at comparatively longer times or higher temperatures, cellular repair mechanisms can no longer keep up or lose function due to the thermal damage of key enzymes, and cell death and tissue necrosis will occur within 3 to 5 days. Different tissues exhibit different levels of sensitivity to thermal damage.

The localization of exposure of high-temperature hyperthermia at temperatures greater than 45° C. to 50° C. can be used to selectively destroy or permanently alter tissue regions. In the high-temperature regime, thermal coagulation and thermal necrosis occurs in tissues exposed to temperatures greater than 50° C. to 55° C. for a duration of 1 to 2 minutes or shorter times at even higher temperatures. The thermal exposure of tissues to high temperatures causes many cellular and tissue structural proteins to undergo irreversible denaturation and conformational changes. These thermal effects are lethal and immediate, producing thermally coagulated (dead) tissue.

On the extreme end, temperatures close to or greater than 100° C. generate less subtle effects, such as explosive vaporization and ablation of tissue. Varying degrees of high temperature thermal therapy are used for cancer therapy, treatment of cardiac arrhythmias, treatment of benign disease (BPH, uterine and breast fibroids), snoring, cosmesis, tissue modification, treatment of sports injuries, etc. However, the efficacy of these treatment modalities may be limited due to inadequacy in protecting sensitive non-targeted tissues or adequately treating a large enough of a volume of tissue.

One example of an organ that responds well to various forms of thermal therapy is the prostate gland. Benign prostatic hyperplasia (BPH) is a frequent benign disease that often requires surgical intervention. Prostate cancer affects 250,000 men annually. Surgery and radiation therapy are the common forms of treatment for prostate cancer. Numerous biological and clinical investigations have demonstrated that heat treatments within the 41° C. to 45° C. range can significantly enhance clinical responses to radiation therapy, and has the potential for enhancing other therapies such as chemotherapy, immunotherapy, and gene therapy as well.

Furthermore, high temperature hyperthermia (greater than 50° C.) alone may be used for selective tissue destruction as an alternative to conventional invasive surgery (Transurethral Resection, or TURP). Thermal techniques can also be utilized to complement existing courses of treatment or provide a minimally invasive alternative to surgery with less complications, and morbidity for each of these diseases. Additionally, transurethral, transrectal, and interstitial systems that use RF currents, lasers, microwaves, ultrasound, and thermal conduction heating technology, can be implemented in the clinic or under development for this type of therapy.

Presently, treating the prostate gland with heat is problematic. The most significant clinical experience to date includes treatment of BPH with transurethral microwave devices. If properly positioned within the prostatic urethra, these devices can thermally destroy a region within the center of the prostate, which leads to a reduction of BPH symptoms. Improvements to these devices and clinical protocols are directed towards decreasing treatment time and destroying larger amounts of tissue in a more precise manner. Although moderately effective for treatment of BPH, these devices are not effective for treating prostate cancer, which mostly involves tissues away from the urethra in the posterior portion of the gland, often adjacent to critical nerves and the rectum. In order to treat large distances from the urethra, higher amounts of energy and greater temperatures are required, leading to damage of the rectum or surrounding non-targeted tissues. Precise techniques for localizing or depositing energy within the gland are required for the treatment of cancer. Transrectal focused ultrasound devices (HIFU) offer some spatial control but treating the most dorsal portion of the prostate is still problematic, due to the risk of thermal damage to the rectum. New developments in transurethral ultrasound heating technology have demonstrated precise, directed and extensive heating capabilities in the anterior and lateral prostate tissue. Large volumes of tissue can be heated in the posterior margin of the prostate gland, but extreme care needs to be undertaken to avoid damage to the rectum and other non-target tissues. The potential exists to heat the entire prostate with transurethral ultrasound if the rectum tissue can be protected and incident energy can be reflected back to the prostate. Interstitial approaches (needle implantation) provide another method of localizing heating energy, but only interstitial ultrasound has the capability of directional heating patterns to avoid the rectum and surrounding bone.

A second example of effective thermal therapy is in the treatment of gynecological diseases. Gynecological diseases treated by thermal therapy typically include menorrhagia, uterine and cervical cancer, and uterine fibroids. In the case of menorrhagia, different heating modalities are placed directly within the os of the uterus and heating energy is applied. For fibroids, interstitial lasers and RF energy have been applied to thermally destroy the tissues. New developments in ultrasound heating technology are also leading to external, intracavitary, and interstitial techniques that promise better localization. The amount of heating power, temperature distributions, and applicator placement are often limited in the treatment of these diseases by the need to protect sensitive non-targeted tissues.

Thus it can be seen that the usefulness and efficacy of thermal therapies are limited by the sensitivity to thermal exposure of associated non-target tissues. The usefulness and efficacy of treatments other than thermal therapy, such as interstitial and external beam radiation therapies, may also be limited by the collateral damage to non-target tissues that can occur with these therapies.

Some other cancer therapies include the placement of small radiation sources into the tumor using specialized catheters in a procedure called brachytherapy. For example, low dose rate brachytherapy (LDR) includes the permanent implantation of radioactive "seeds" of gold or iodine into the tumor or organ tissues. The implanted seeds give off radiation in low doses over a period of several months and remain in the organ permanently. A typical LDR brachytherapy procedure for prostate cancer may include the placement of over 100 radioactive implants in the prostate gland of the patient.

A second brachytherapy procedure was developed, known as high dose rate brachytherapy (HDR), which uses precisely positioned catheters at tumor sites. High dose radiation sources are then sent to the tumor sites through the catheters and removed from the body after a period of time and are temporary implants. Thus, a high dose of radiation can be directed to the cancerous tumor for a time and removed. However, proper placement of the HDR catheters is critical because of the high dosages of radiation involved.

Prostate adenocarcinomas for example, are particularly well suited for both LDR and HDR brachytherapy procedures. The three dimensional visualization of the placement of 125-Iodide seeds during transperperineal implantation, for example, has recently been accomplished with the use of transrectal ultrasonography ("TRUS"). Unfortunately, the imprecise placement of radiation sources can still occur with the use of ultrasound due to the proximity of the bladder and rectum and associated structures to the prostate gland. For both of these forms of interstitial radiation therapy, computer treatment planning is performed to produce a specific radiation dose distribution encompassing the target regions, and includes a safety margin around sensitive structures such as the rectum. For many cases, especially treatment of a previously radiated recurrence, the total radiation dose that can be applied is limited due to the exposure limits on normal tissue structures that are close to the prostate gland such as the rectum, bladder and urethra. For prostate and uterine tissue, this translates to a limited radiation treatment in the posterior portion of the organ in proximity to the rectum.

Accordingly, there is a continuing need in the art for a device or procedure that can apply thermal or radiation therapy to the target tissue or tumor while insulating or positioning associated sensitive structures to modify exposure to radiation or thermal treatments and enhancing diagnostic imaging. The present invention satisfies these needs, as well as others, and generally overcomes the deficiencies found in existing equipment and methods.

BRIEF SUMMARY OF THE INVENTION

The present invention generally comprises a catheter with one or more small deployable balloons, bladders, or expandable membranes that may be inserted into the body using common implant techniques known in the art. By way of example, and not of limitation, in accordance with one aspect of the invention, a catheter having a central lumen is provided with a balloon attached to the catheter shaft and the interior of the balloon is in fluid communication with the central lumen. In one embodiment, a second lumen in the catheter provides a conduit for an electrical connection to a number of temperature sensors disposed in or on the balloon. The temperature sensors provide a general indication of the thermal exposure of tissues and structures surrounding the target tissues. In another embodiment the temperature sensors indicate the local temperature of the target tissue during treatment. In another embodiment the sensors detect localized radiation exposure.

The balloons may be provided in various predetermined shapes and points of adhesion to the catheter and may be folded prior to insertion depending on the procedure. Gas or liquid is then introduced through one of the central lumen (s) and into the balloon thereby inflating the balloon after placement of the catheter in the body.

In an alternative embodiment, the catheter has an input lumen(s) and an output lumen(s) that have input and output ports to and from the interior of the balloons. Fluid introduced to the input lumen enters the interior of a balloon through the input port causing it to inflate. The fluid in the balloon can be cycled by removing fluid from the balloon through the output port and output lumen. With this embodiment, a gas can be initially introduced to the balloon and then later a liquid can be cycled through the system replacing the gas. Also depending upon the procedure, gas can be interchanged for the fluid, or varying levels of gas and fluid can reside within same device or balloon or compartment. One medium can also be used to purge the other.

In another embodiment, multiple balloons may be positioned on the catheter and are connected with a common lumen so that the balloons inflate simultaneously when a fluid or gas is introduced into the input lumen. In another embodiment, the catheter has multiple balloons with a separate controlling set of communication lumens associated with each balloon. In this embodiment, each balloon may be independently filled with different material at different levels of inflation at different times as needed.

In an embodiment configured for use with treatment of the prostate, the catheter is inserted in the space between the prostate and the rectum and then inflated. The placement of multiple catheters can also be applied as part of this treatment. Inflation of the balloon(s) physically separates the thermal and radiation sensitive rectum tissue from the prostate gland being treated, and thereby providing a level of thermal insulation. The fluid filled balloon may act as a heat sink to draw heat away from the sensitive tissues. The fluid may also be introduced at a temperature below the temperature of the body of the patient.

The fluid filled balloon may also act as a radiation absorber or transmitter to reduce or modify exposure to the sensitive tissues. Also, the gas or fluid inflating the balloon may act as an acoustic insulator or the fluid may act as an acoustic conductor as desired during diagnostic and treatment stages of the underlying procedure.

In one embodiment, either a gas or a fluid with an acoustic mismatch from surrounding tissue or an acoustic absorber is used to inflate the balloon(s) and thereby modify the acoustic transmission and reflective characteristics between the tissue and the device.

In another embodiment, membrane material and fluid is selected for levels of electromagnetic mismatch from tissue or electromagnetic absorber is filled in balloon(s) to modify the electromagnetic transmission and reflective characteristics between tissue and device.

In yet another embodiment, membrane material and fluid is selected for levels of electrical impedance mismatch from tissue or electrically conductive or resistive material is filled in balloon(s) to modify the electrical transmission characteristics between tissue and device.

In still another embodiment configured for use with HDR brachytherapy procedures, one or more catheters are placed between the target organ and the organs or structures in proximity to the target tissue. The balloon is inflated with a gas or fluid to physically position or separate the organs or tissues and thereby modify the exposure of surrounding structures during treatment of the target tissue. The fluid can be of the type to transmit or absorb radiation.

In another embodiment, the interior of the balloon has a partition separating the interior of the balloon into two chambers. One chamber may be filled with a liquid and the other chamber filled with a gas in this embodiment.

The catheter material may be hard or soft or rigid or flexible depending on the desired application. The tip of the stiff catheter may be sharp to allow for the direct insertion into tissue. The catheter tip may also be blunt and may be configured for placement with a removable stiffener or introducer. Flexible material such as silicone will allow for a longer duration implantation and longer balloon deployment such as with permanent seed implant.

An object of the invention is to provide an apparatus and method of thermally insulating organs and tissues from the target tissue of a thermal therapy procedure.

Another object of the invention is to provide an apparatus and method of insulating organs and tissues from the target tissue of an external radiology or brachytherapy procedure.

Another object of the invention is to provide an apparatus and method of blocking the exposure of sensitive surrounding tissues to acoustic energy from the target tissue.

Another object of the invention is to provide a catheter that has one or more deployable balloons with one or more lumens that have varied shapes and sizes that can conform to natural spaces or expand to a predetermined shape between internal body organs or tissues.

Still another object of the invention is to provide a catheter that has a variety of sensors that can allow the monitoring of temperature, radiation dose or other localized conditions.

Another object of the invention is to provide an apparatus that can provide fluid to inflate a balloon to selectively isolate target tissues.

Another object of the invention is to provide an apparatus that can circulate fluid within the inflated balloon.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings that are for illustrative purposes only:

FIG. 1 is longitudinal cross-section of the distal tip section of one embodiment of the catheter after inflation of the balloon in accordance with the present invention.

FIG. 2 is transverse cross-section of the catheter shaft of the embodiment of the invention taken along the lines 2—2 shown in FIG. 1.

FIG. 6 is a transverse cross-section of an alternative embodiment of the catheter shown in FIG. 5.

FIG. 7 is a transverse cross-sectional view of an alternative embodiment of the catheter of the present invention.

DETAILED DESCRIPTION OF THE INVENTION

Figure 3:
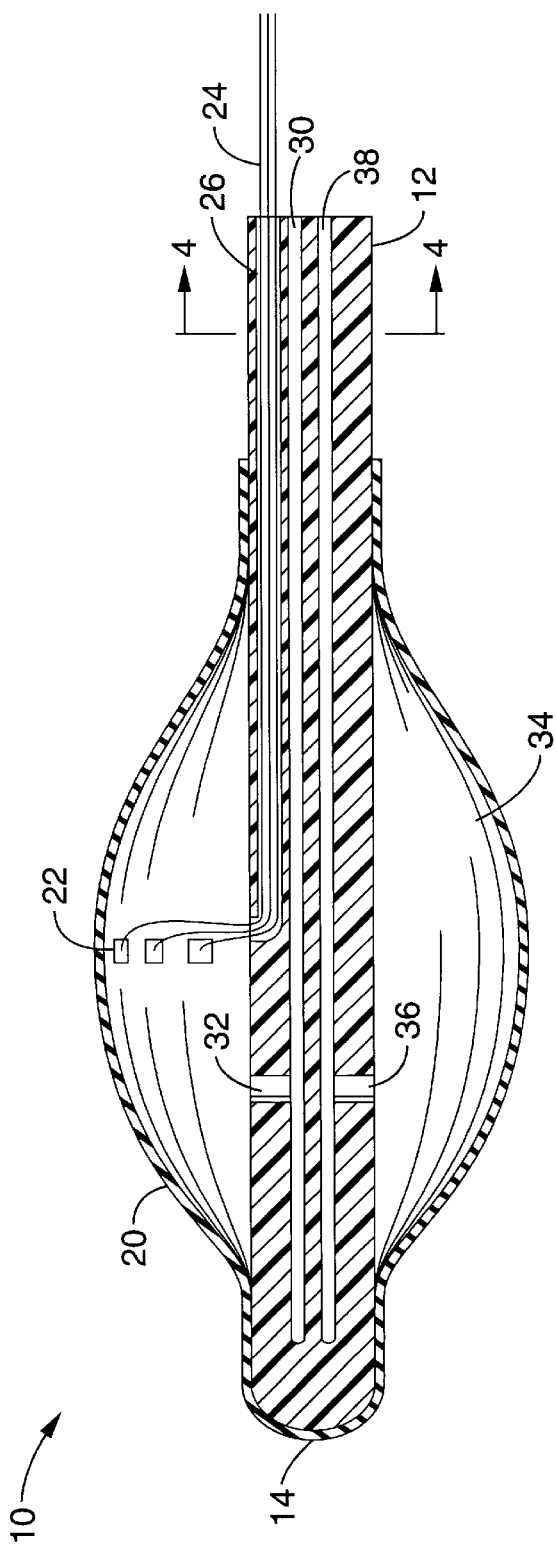
FIG. 3 is a longitudinal cross-section of an alternative embodiment of the catheter of the preset invention with intake and outtake lumens.

Referring more specifically to the drawings, for illustrative purposes the present invention is embodied in the apparatus and methods generally shown in FIG. 1 through FIG. 10. It will be appreciated that the apparatus may vary as to configuration and as to details of the parts, and that the methods may vary as to the specific steps and sequence, without departing from the basic concepts as disclosed herein.

Referring first to FIG. 1 and FIG. 2, the invention comprises a positioning catheter 10 with a catheter shaft 12 and tip 14 constructed for insertion into the body of a patient. The catheter shaft 12 and tip 14 may alternatively be configured to be inserted into tissue using a separate needle introduction catheter that is removed after insertion and provides protection to the components of the device during insertion. The apparatus may be used interstitially as well as laproscopically or endoscopically during procedures in the joints, abdomen, esophagus or uterus/cervix etc. The apparatus may be configured for short term or long-term placement in the body. The apparatus is particularly suited to protect sensitive tissues or structures in proximity to target tissues for thermal or acoustic treatments. Additionally, the insertion of the catheter 10 and the balloon inflation may be monitored using ultrasonic diagnostic imaging, CT fluoroscopic imaging, magnetic resonance imaging (MRI), or other appropriate means for visualization known in the art.

Catheter shaft 12 is preferably manufactured from polyethylene, polystyrene, polycarbonate, polyamide, silicone, rubber or similar flexible tubing. Alternatively, the catheter shaft 12 may be thin walled stainless steel hypodermic tubing or the like that provides an independent structural support and integrity for direct insertion into tissue.

In the embodiment shown, the catheter shaft 12 has at least one central lumen 16 running the length of the shaft 12 that allows the flow of liquid or gas from the proximal end to the distal end of the catheter 10. Fluid from the lumen 16 flows through ports 18a, 18b in the walls of shaft 12 to the interior of balloon 20 thereby inflating balloon 20. Fluid may be introduced to lumen 16 of the proximal end of the catheter shaft 12 by a syringe or pump (not shown) that is connected and sealed to the catheter shaft 12. A syringe or pump that is capable of delivering a determined volume of gas or liquid at a desired pressure is preferred to provide a consistent and predictable expansion of balloon 20. The lumens may also be operably connected to valves known in the art to regulate the flow into and out of the catheter. In one embodiment, the shaft 12 may have a lumen that exits the tip of the shaft to allow the introduction of medications or the like directly to the placement site.

The fluid directed to balloon 20 is preferably non-toxic and non reactive with the balloon or catheter material such as water, oil, diagnostic imaging agents or saline solution. Gases preferably used to inflate balloon 20 include air and perfluorocarbons or the like. The fluid may also be a combination of liquid and gas.

Balloon 20 preferably comprises a flexible material such as polyethylene, polyester, polyvinyl, Mylar, silicone, latex, polyurethane, C-flex or other appropriate material. The walls of balloon 20 are preferably thin enough to collapse to a small volume around the catheter shaft 12 for easy insertion yet durable enough to withstand relatively high pressures upon inflation. In one embodiment, the balloon material is a porous membrane that may allow movement of saline or other material across the membrane and may conduct an electric current. In another embodiment, balloon 20 is made of an inelastic material that will inflate to a predetermined shape. That shape may be the shape of the target tissue, tissue space or organ. In yet another embodiment, balloon 20 has a metallized surface that is capable of conducting electrical current. Balloon 20 may also be manufactured of material that optically blocks or is optically transparent to laser or infrared light.

It will be appreciated that the invention is not limited to a one-balloon configuration. If desired, more than one balloon may be affixed circumferentially around shaft 12 with fluid ports communicating with the central lumen 16 to allow the simultaneous inflation of the balloons. Thus, a linear array of balloons can be used to raise and separate tissues and organs during use.

Balloon 20 may also be configured to inflate to shapes that are lobed, spoon-shaped, generally planer, asymmetrical or any desired shape that will displace tissues or organs to the preferred positions, and provide treatment modification, protection, or thermal control. The size of the balloon 20 is also variable depending on the size of the organ to be displaced and the type of displacement required. Additionally, balloon 20 may also be compartmentalized or chambered such that each chamber can be inflated independently of the other and with different fluids. Balloon 20 may also be configured to have secondary balloons emanating from a primary balloon or balloons.

Optionally, balloon 20 can have a number of miniature sensors 22 coupled to leads 24. The leads 24 are preferably disposed in a longitudinal lumen 26 in the catheter shaft 12 and connect the sensors to appropriate machines outside of the body. For example, sensors 22 may be miniature thermocouples that can measure the temperature of the balloon, external tissue or inflation liquid temperatures. Sensors 22 may also be capable of detecting radiation exposure or the like such as a TLD radiation dosimeter. Sensor 22 may also be a fiber optic sensor or a thermistor. Sensors 22 such as dosimeter chips may also be interpreted when the catheter is removed from the body. Accordingly, the sensors 22 can be configured to measure the temperature of the target tissue, the non-target tissue of the fluid media inflating the balloon 20 as well as radiation exposure.

Figure 4:
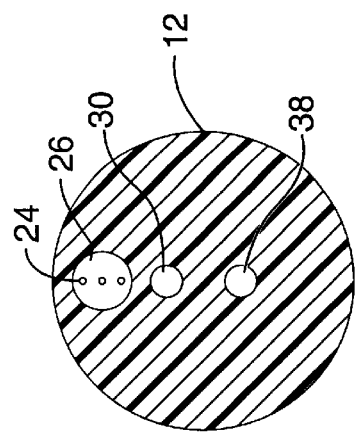
FIG. 4 is transverse cross-section of the catheter shaft of the alternative embodiment of the invention taken along the lines 4—4 shown in FIG. 3.

Turning now to FIG. 3 and FIG. 4, an alternative embodiment of the invention is shown. This embodiment is preferably configured to circulate the fluid that inflates the balloon 20 under constant pressure so that the balloon 20 maintains its shape during fluid circulation. Changes in pressure of the inflation liquid may modify the shape of the balloon 20 through expansion or contraction in an embodiment with a balloon 20 made of elastic material. However, embodiments with balloons 20 made of inelastic material may maintain the shape of balloon 20 with increases in fluid pressure over the minimum pressure required to inflate the balloon 20.

In the embodiment shown, catheter 10 has a catheter shaft 12 that has two lumens 30, 38 running longitudinally the length of the shaft 12. Lumen 30 serves as an input lumen and is in fluid communication with one or more input ports 32 that exit to the interior of balloon 20. Thus, gas or fluid passes through lumen 30 and port 32 into the interior 34 of balloon 20 inflating the balloon.

The liquid or gas from the interior of the balloon 20 can be cycled through the interior 34 of the expanded balloon 20 through output port 36 and into output lumen 38 and back to the proximal end of the catheter 10. Valves (not shown) and other pressure regulation devices known in the art can regulate the pressure of the liquid or gas entering and exiting a given set of lumens during circulation.

The use of input lumen 30 and output lumen 38 also allows the sequential introduction of different media to the balloon 20. For example, a fluid can be first introduced during placement so that diagnostic imaging can be used to verify balloon deployment. Next, an inert gas or air could then introduced to lumen 30 to ports 32 to inflate balloon 20. The gas in the balloon 20 can act as an acoustic barrier to ultrasonic waves and provide acoustic isolation to the surrounding tissue. At the end of the procedure or when the sensors 22 indicate elevated tissue temperatures, the gas in lumen 30 and balloon 20 can be flushed through output port 36 and output lumen 38 by introducing water or oil or some other appropriate liquid into lumen 30. The liquid is preferably introduced to lumen 30 at the same pressure and volume as the gas so that the balloon 20 does not deflate during the transition. The liquid can act as a heat sink to draw the heat from sensitive tissues in physical contact with the balloon 20 and/or transmission of acoustic imaging or reduction of artifacts in diagnostic imaging. This process can be repeated if necessary.

In one embodiment, the fluid is cycled in a closed loop at a controlled pressure with a pump (not shown) coupled between the intake lumen 30 and the exit lumen 38. The pump is preferably capable of monitoring the pressure and volume of fluid introduced to the input lumen 30.

In another embodiment, the closed fluid loop has a cooling or heating device that reduces or elevates the temperature of the liquid cycling through the system and into lumen 30 and the balloon 20. Accordingly, in the embodiment shown, the sensors 22 may monitor the temperature of the liquid at the balloon 20 or the temperature of the tissue and cool or heat the liquid to a specified temperature.

Figure 5:
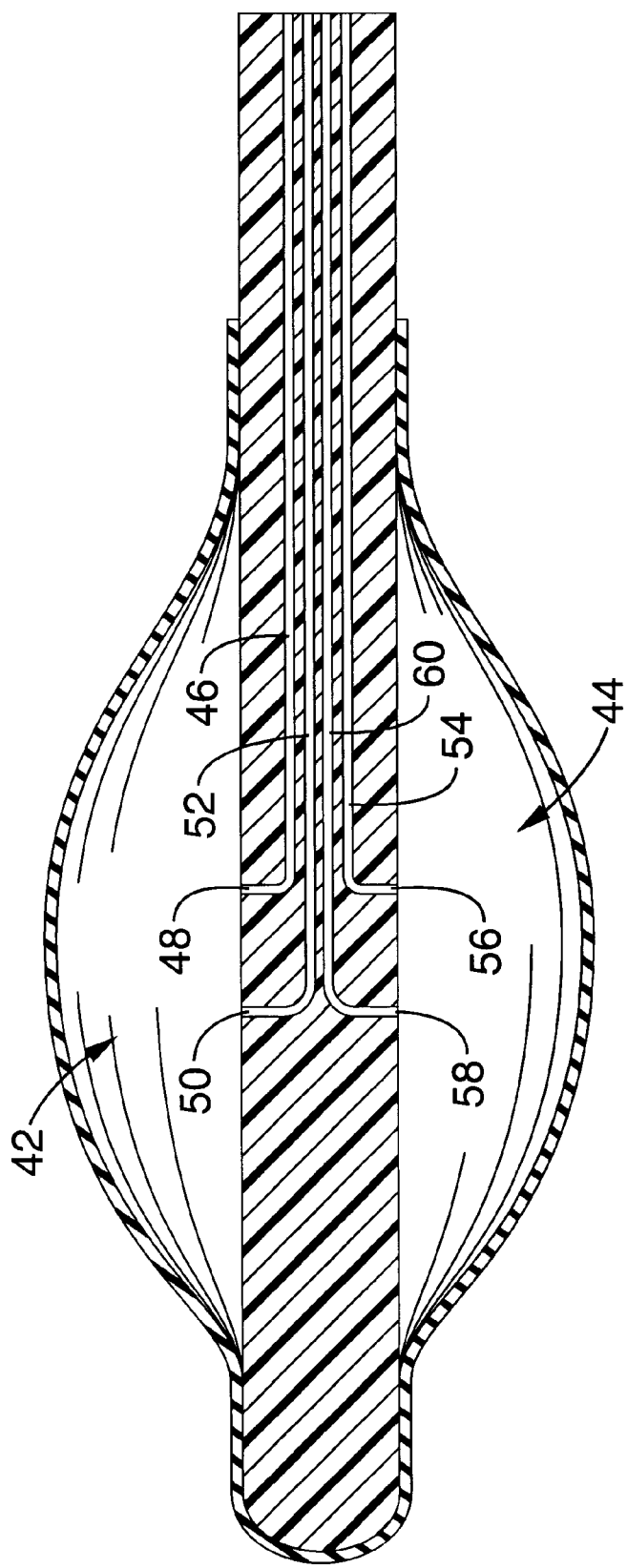
FIG. 5 is a longitudinal cross-section of an alternative embodiment of the catheter of the present invention showing two sets of intake and output ports.

Referring now to FIG. 5 and FIG. 6 an alternative embodiment of the catheter is shown. In this embodiment, the interior of the balloon is divided into discreet sections by a partition 40. The partition 40 creates two chambers 42, 44 within the balloon. While the embodiment shown has one partition, it will be understood that more than one partition may be used. Each chamber 42, 44 are fed by a set of input and output lumens that permit selective inflation of the chamber and cycling of fluid into the chamber. For example, a gas could be introduced into chamber 44 through input lumen 46 and input port 48 to inflate chamber 44. The gas may be cycled through output port 50 and output lumen 52. At the same time or subsequently, chamber 42 may be filled with water through input lumen 54 and input port 56. It can be seen the two different types of media can be used to isolate target tissues from sensitive non-target tissues. After the procedure, the chambers 42, 44 of the balloon can be deflated by removing the contents of chamber 42 through output port 58 and lumen 60 and the contents of chamber 44 through output port 48 and lumen 46. Thus, the user of the catheter of the present invention can isolate non-target tissues from target tissues with different media at different times during the course of the treatment. Media that is particularly suitable for visualization of the catheter for placement may be exchanged for media that is radio opaque or acoustically opaque for use during treatment.

Turning now to FIG. 7, it can be seen that the balloon element of the catheter can have a variety of configurations. The embodiment shown in FIG. 7 allows for inflation of the balloon to a generally planar configuration. Upon inflation, the central element 62 receives fluid from a central lumen 64. One or more conduits 70 connect the central element 62 to two adjoining chambers 66a and 66b that allow fluid communication from the central element 62 and inflate the chambers 66a, 66b. There are one or more conduits 72 connecting chambers 66a, 66b with 68a, 68b respectively such that the chambers are in fluid communication with each other. As seen in FIG. 7, the sequential inflation of paired chambers can provide a planar separation of the target and non-target tissues as well as insulation of the tissues with the use of appropriate fluid media to inflate the apparatus.

Figure 8:
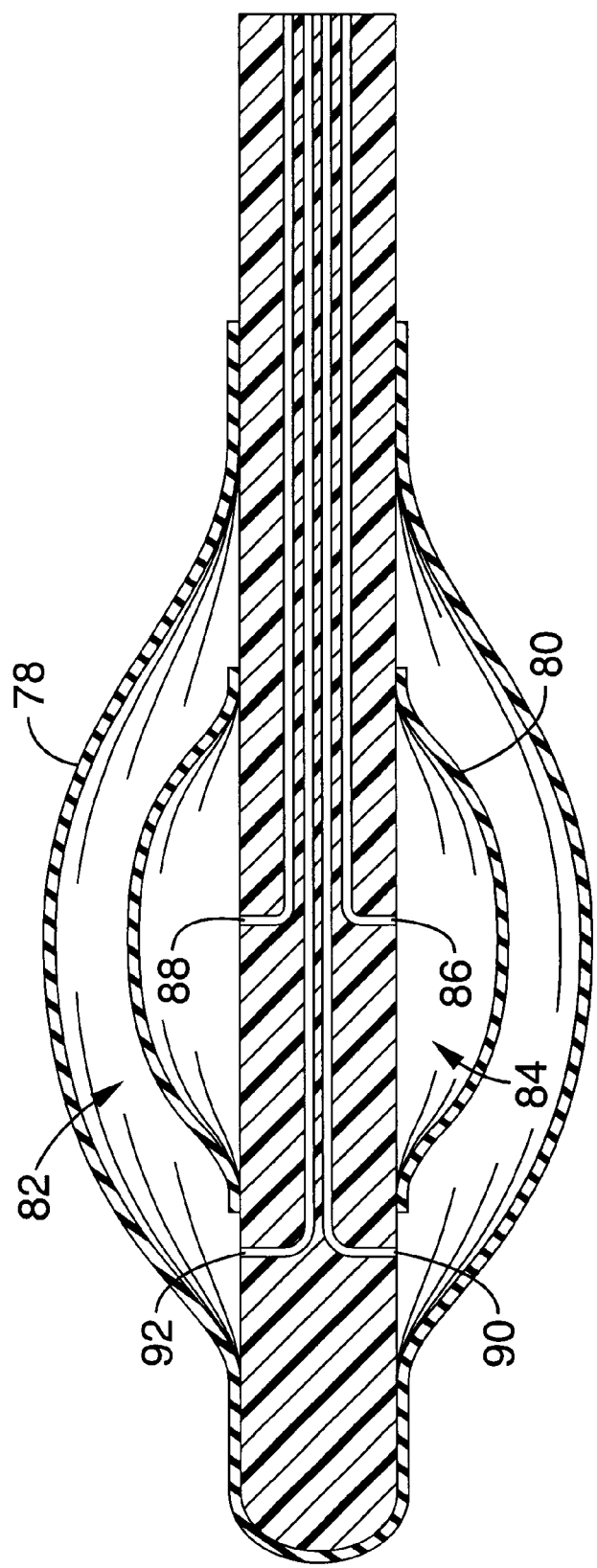
FIG. 8 is a longitudinal cross-sectional view of an alternative embodiment of the catheter of the present invention showing a balloon within a balloon and associated ports and lumens.

Another alternative embodiment of the apparatus having a balloon within a balloon configuration is shown in FIG. 8. In the embodiment shown, there is an outer balloon 78 that is attached to the shaft of the catheter. Within the outer balloon 78 is an inner balloon 80. The outer balloon forms an outer chamber 82 and the inner balloon forms an inner chamber 84. The inner balloon 80 and the outer balloon 78 can be inflated independently of the other in the embodiment shown in FIG. 8. It can be seen that the inner balloon 80 can be inflated by the insertion of fluid through input lumen and port 86 and cycled through output port 88. Alternatively, ports 86 and 88 may be used as input ports and output ports simultaneously to inflate and deflate balloon 80. The outer balloon can be inflated by the insertion of fluid into the outer chamber 82 through the input lumen and port 90 and cycled through output port 92. In this embodiment, for example, the catheter apparatus could be placed at the desired location in the body and a gas introduced into inner chamber 84 to facilitate acoustical imaging to insure proper placement. Outer balloon 78 may then be inflated by filling the outer chamber 82 with a fluid such as a diagnostic imaging agent that is capable of insulating non-target tissues from various forms of radiation. If desired, the gas in chamber 84 of inner balloon 80 can be exchanged for a chilled fluid such as water or oil that can be cycled through input port 86 and output port 88 to manipulate the local temperature at the catheter balloon site.

Figure 9:
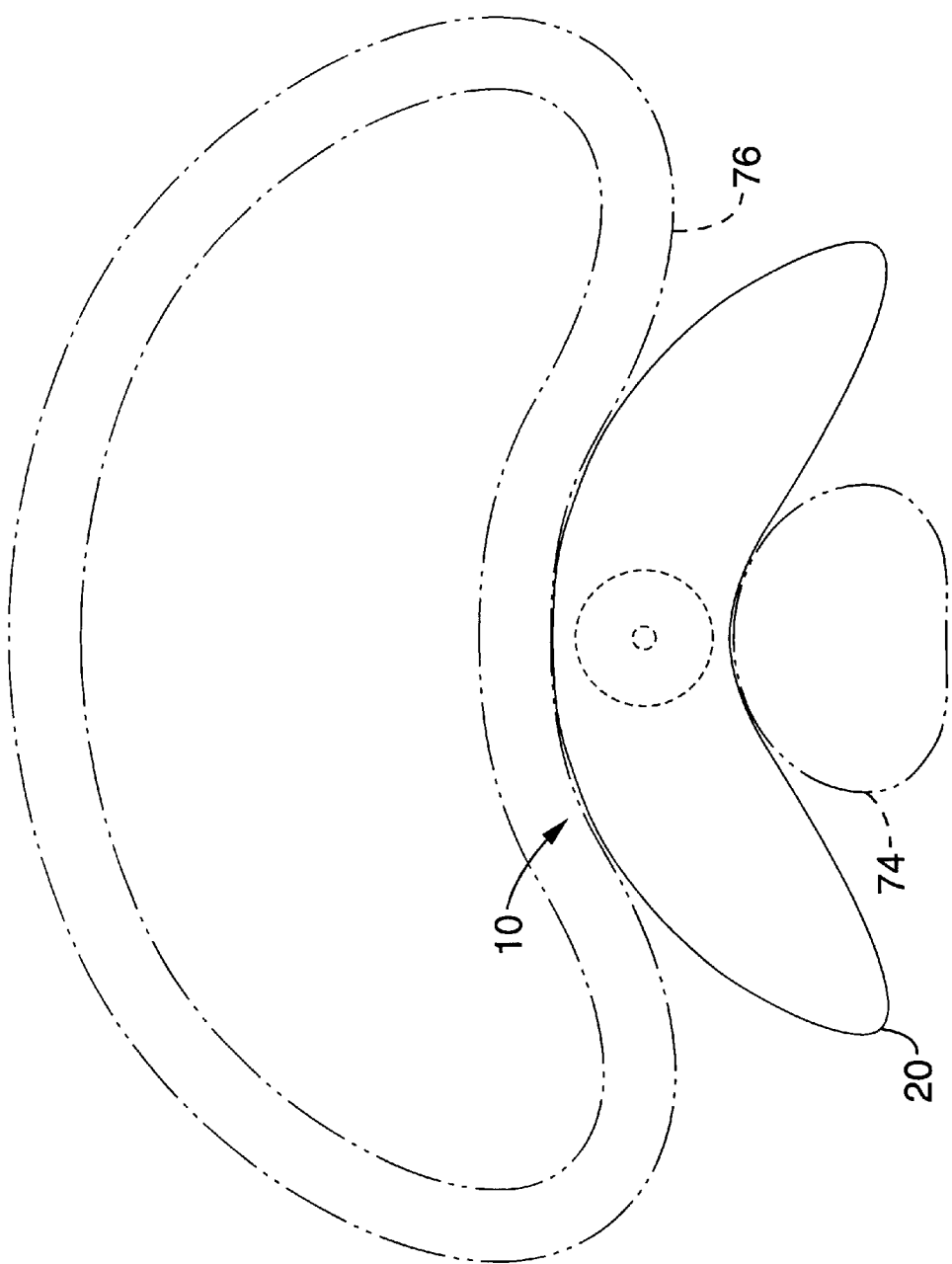
FIG. 9 is a front view of one embodiment of the invention positioned between the target tissue and a surrounding tissue.
Figure 10:
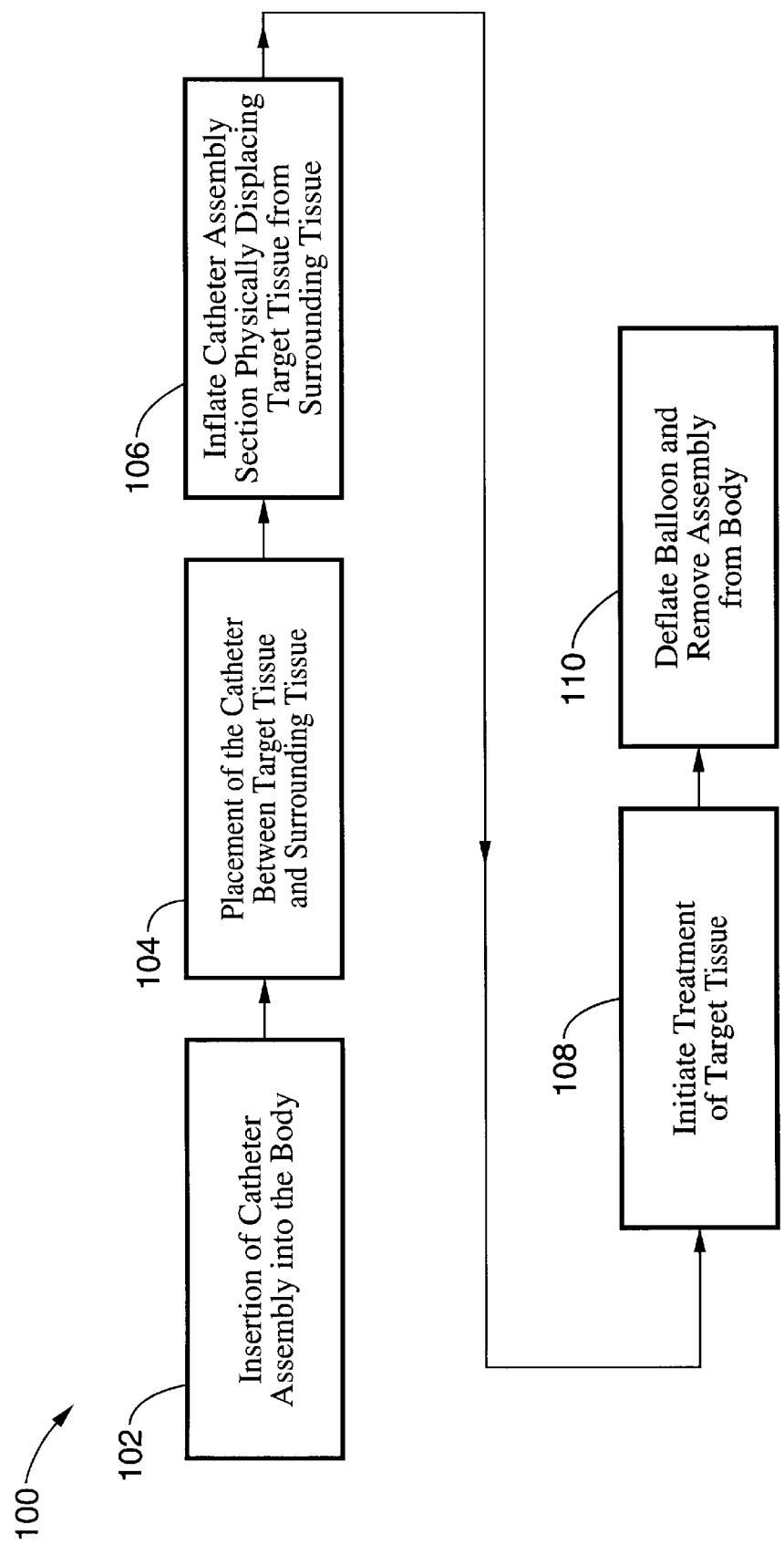
FIG. 10 is a flow diagram showing generally the method steps in one embodiment of a method for isolating a target tissue or organ from surrounding tissues or organs during treatment of the target organ.

Referring now to FIG. 9 and FIG. 10, the method for treatment 100 of a diseased tissue site utilizing the apparatus of the present invention can be illustrated with a specific exemplary condition, benign prostate hyperplasia. The first step 102 for treatment of the prostate after diagnosis and preparation for conventional surgical procedure is to insert the catheter of the present invention into the body and locate the virtual space between the target prostate gland and the structures in proximity to the target gland. The prostate is located under the bladder and in front of the rectum. Visualization of the organs and structures of the body and the catheter can be accomplished with ultrasound, CT, fluoroscopic imaging or other imaging techniques known in the art.

The second step 104 is to place the catheter 10 at the boundary of the treatment site and the healthy tissue or sensitive tissues or structures that may be damaged during treatment of the target tissue. In the example shown, the catheter 10 is placed in the virtual space between the rectum and the prostate.

The third step 106 is to inflate the balloon member 20 to physically displace the diseased target tissue and the surrounding critical tissues or structures. The balloon 20 will physically displace the prostate organ from the rectal wall in the example provided. In many instances the separation that occurs between target and sensitive tissues need only be a few millimeters to effectively insulate the sensitive tissues. The selection of the gas or liquid that inflates the balloon 20 as well as the size and number of balloons on the catheter 10 will depend on the type of treatment that is to be performed on the target tissue. For example air or gas may be used to inflate balloon 20 to block or deflect acoustic energy directed toward sensitive tissues from the target organ or elsewhere. The placement and inflation of one embodiment of the catheter between the target tissue 74 such as the prostate gland and the sensitive non-target tissue 76 such as the rectum can be seen in FIG. 9.

The fourth step 108 is to initiate and complete the treatment on the target tissue once the target tissue is isolated from sensitive tissues by the catheter assembly. Thermal therapy procedures of the prostate gland may have radio frequency, laser, ultrasound, microwave or other energy sources to elevate the temperature of the prostate. In one embodiment, the localized temperature of the target tissue and the proximal tissues is monitored during the procedure with temperature sensors on the outside or inside of the balloon. Alternatively, the temperature of the liquid within the balloon may be monitored.

In another embodiment, cycling thermally conductive fluid through the catheter assembly and balloon 20 to draw off heat from the heat sensitive structures may reduce the temperature of the sensitive structures. Alternatively, fluids with a temperature lower than body temperature can be cycled through the assembly 10 to quickly cool the structures engaged with the balloon and catheter assembly 10.

In still another embodiment, during cryogenic treatments, the fluid that is cycled within the catheter assembly 10 is preferably greater than body temperature. The pressure, temperature, volume and flow through the balloons 20 may be dynamically controlled during treatment.

The fifth step 110 is the deflation of balloon 20 and the removal of the catheter assembly from the patient. In one embodiment, the fluid in the catheter 10 is cycled and cooled to keep the temperature sensitive rectum at an appropriate temperature and to reduce the temperature of the target tissues after treatment.

Referring again to FIG. 10, a second example of the method for treatment 100 of a diseased tissue site utilizing the apparatus of the present invention can be shown in treatment of prostate cancer using LDR seed implants or HDR brachytherapy. After diagnosis, the insertion of the catheter of the present invention into the body for placement into the space between the target prostate tissue and the surrounding sensitive non-target tissues is accomplished in step 102. The radioactive seeds or HDR brachytherapy catheters may be implanted before or after the placement of the catheter in the body as provided in step 102.

Placement of the catheter at the boundary between the target and non-target tissues in step 104 may be facilitated by the use of ultrasound, CT, fluoroscopic imaging or the like. The introduction of small amounts of a radio-opaque or an acoustically opaque gas or liquid into the catheter assembly may assist in the proper placement of the catheter between target and non-target tissues.

The third step 106 is to inflate the balloon member to physically displace the target tissue from the non-target tissues. In this example, the LDR seed implants are long term implants in the prostate exposing the surrounding sensitive tissues such as the rectum to long-term exposure to radiation. Alternatively, the HDR brachytherapy implants are shorter term implants in the prostate exposing the surrounding sensitive tissues such as the rectum to high-doses of radiation. Accordingly, the catheter 10 and balloon 20 are configured for permanent or long term or short term placement. The balloon 20 may be filled with material that will provide a barrier to, or modification to, the radiation dose from the seed implants or direct radiation sources. The balloon 20 may also be shaped to reflect radiation back into the prostate gland or other target structure and away from surrounding tissues or move the surrounding non-target tissue to a particular position.

The fourth step 108 is to initiate and complete treatment on the target tissue. The catheter and balloon apparatus may be kept in position during the majority of the LDR seed therapy or HDR brachytherapy to protect the surrounding tissues as well as protect and shape the treated tissues during therapy. In one embodiment, different media can be cycled through the balloon during diagnostic imaging and treatment.

Removal of the catheter after deflation of the balloon is accomplished in the fifth method step 110. In the present example, the balloons may be deflated by removing the gas or liquid media from the interior of the balloons. In one embodiment, the materials comprising the catheter and balloon are biologically inert and remain in the body permanently.

Accordingly, it will be seen that this invention provides a simple and effective apparatus and method for isolating treated organs and tissues from thermal or radiation sensitive tissues and structures for treatment. Although the description above contains many specificities, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A system for minimally invasive therapy modification of tissue to be treated in a localized prostate therapy procedure in a patient, comprising:

an energy source configured to deliver sufficient energy into a region of target tissue associated with a prostate in the patient to provide a therapeutic result;

an elongated shaft having at least one lumen extending therethrough;

inflatable means coupled to an end of said shaft for separating the target tissue from a region of adjacent tissue associated with a rectum in the patient and that is located adjacent to the target tissue, and also for substantially isolating the adjacent tissue from the energy delivered from the energy source and into the target tissue; and wherein the tissue effects on the adjacent tissue from the energy delivered into the target tissue from the energy source are substantially modified by the inflatable means.

2. A system as recited in claim 1, wherein said inflatable means comprises a balloon.

3. A system as recited in claim 1, further comprising a temperature sensor coupled to said inflatable means and configured to sense temperature of said target tissue and said adjacent tissue.

4. A system as recited in claim 1, further comprising a radiation sensor coupled to said inflatable means and configured to sense exposure of said target tissue and said adjacent tissue to radiation.

5. A system as recited in claim 1, further comprising means for inflating said inflatable means.

6. A system as recited in claim 5, wherein said means for inflating comprises:

a fluid disposed within said at least one lumen; and means for moving said fluid through said lumen to said inflatable means, wherein said inflatable means is inflated.

7. A system as recited in claim 6, wherein said means for moving said fluid comprises a syringe and a valve.

8. A system as recited in claim 6, wherein said fluid comprises a liquid, or a gas or a mixture of a liquid and a gas.

9. A system as recited in claim 6, wherein said means for moving fluid further comprises means for cycling said fluid through said lumens of said shaft and said inflation means.

10. A system as recited in claim 1, wherein:

the energy source comprises a radiation source adapted to deliver a therapeutic amount of radiation energy into the target tissue; and the inflatable means comprises means for substantially isolating the adjacent tissue from the therapeutic amount of radiation energy delivered into the target tissue from the radiation source.

11. A system as recited in claim 1, wherein:

said energy source comprises an ultrasound energy source configured to deliver a therapeutic amount of ultrasound energy to the target tissue; and said inflatable means comprises means for substantially isolating the adjacent tissue from the therapeutic amount of ultrasound energy delivered into the target tissue from the ultrasound energy source.

12. A system for minimally invasive therapy modification of tissue to be treated in a localized prostate therapy procedure in a patient, comprising:

an energy source configured to emit sufficient energy into a region of target tissue associated with a prostate in the patient to provide a therapeutic result;

an elongated shaft having at least one lumen extending therethrough;

an inflatable member coupled to an end of said shaft that is positionable at a location between the target tissue and a region of adjacent tissue associated with a rectum and that is located adjacent to the target tissue; and wherein said inflatable member when inflated at the location is configured to separate the target tissue from the adjacent tissue; and wherein said inflatable member when inflated at the location is further adapted to substantially isolate the adjacent tissue from the energy delivered from the energy source and into the target tissue, such that the tissue effects on the adjacent tissue from the energy delivered from the energy source into the target tissue are substantially modified by the inflatable member.

13. A system as recited in claim 12, wherein said inflatable member comprises a balloon.

14. A system as recited in claim 12, further comprising a temperature sensor coupled to said inflatable member and configured to sense temperature of said target tissue or said adjacent tissue.

15. A system as recited in claim 12, further comprising a radiation sensor coupled to said Inflatable member and configured to sense exposure of said target tissue or said adjacent tissue to radiation.

16. A system as recited in claim 12, further comprising means for inflating said inflatable member.

17. A system as recited in claim 16, wherein said means for inflating comprises:

a fluid disposed within said at least one lumen; and means for moving said fluid through said lumen to said inflatable member, wherein said inflatable member is inflated.

18. A system as recited in claim 17, wherein said means for moving said fluid comprises a syringe and a valve.

19. A system as recited in claim 17, wherein said fluid comprises a liquid, or a gas or a mixture of a liquid and a gas.

20. An apparatus as recited in claim 17, wherein said means for moving fluid further comprises means for cycling said fluid through said lumens of said shaft and said inflatable member.

21. An apparatus as recited in claim 12, wherein said inflatable member further comprises multiple compartments, each compartment capable of inflating independently of the other compartments.

22. A system as recited in claim 12, wherein:

the energy source comprises a radiation source adapted to deliver a therapeutic amount of radiation energy to the target tissue; and the inflatable member when inflated at the location is substantially non-transmissive to radiation energy such that the inflatable member comprises a radiation shield that is adapted to substantially isolate the adjacent tissue from the therapeutic amount of radiation energy delivered into the target tissue from the radiation source.

23. A system as recited in claim 12, wherein:

said energy source comprises an ultrasound energy source configured to deliver a therapeutic amount of ultrasound energy to the target tissue; and said inflatable member when inflated at the location is substantially non-transmissive to ultrasound energy such that the inflatable member comprises an ultrasound shield that is adapted to substantially isolate the adjacent tissue from the therapeutic amount of ultrasound energy delivered into the target tissue from the ultrasound energy source.

24. A system for minimally invasive therapy modification of tissue to be treated in a localized prostate therapy procedure in a patient, comprising:

an energy source configured to deliver sufficient energy into a region of target tissue associated with a prostate in the patient to provide a therapeutic result;

an elongate tubular shaft having a proximal end, a distal end and at least one lumen extending therethrough;

said distal end of said shaft having a tip, said tip and said shaft configured for introduction into a body of a patient;

an inflatable member having an interior and an exterior and that is disposed on said distal end of said elongate tubular shaft;

said inflatable member being positionable at a location between the target tissue and an adjacent region of a rectum located adjacent the target tissue upon introduction of the tip and shaft into the patient's body;

said interior of said inflatable member being open to at least one lumen;

a source of material coupled to the interior;

means for inflating said inflatable member at least in part with the material at the location;

wherein said material is characterized as being substantially non-transmissive with respect to the energy delivered into the target tissue from the source; and wherein said inflatable member when inflated with the material at the location is configured to separate the target tissue from the adjacent tissue; and wherein said inflatable member when inflated with the material at the location is adapted to substantially isolate the adjacent tissue from the energy delivered from the energy source and into the target tissue, such that the tissue effects on the adjacent tissue from the energy emission from the energy source into the target tissue are substantially modified by the material in the inflatable member.

25. A system as recited in claim 24, further comprising a sensor connected to said distal end of said shaft.

26. A system as recited in claim 24, further comprising a sensor connected to said inflatable member.

27. A system as recited in claim 26, wherein said sensor is selected from the group of sensors consisting essentially of a thermocouple, a fiber optic sensor, a thermistor, and a radiation dosimeter.

28. A system as recited in claim 25, wherein said sensor is selected from the group of sensors consisting essentially of a thermocouple, a fiber optic sensor, a thermistor, and a radiation dosimeter.

29. A system as recited in claim 24, wherein said inflatable member comprises a plurality of balloons connected to said distal end of said shaft and configured for substantially simultaneous inflation or deflation.

30. A system as recited in claim 24, wherein:
said inflatable member comprises a plurality of balloons connected to said distal end of said shaft;
each of said balloons is in fluid communication with at least one of said lumens; and
each of said balloons can be selectively inflated or deflated.

31. A system as recited in claim 24, further comprising:
a fluid disposed in said lumen of said shaft;
wherein fluid flow into said lumen causes said inflatable member to inflate; and
wherein said fluid flow delivers the material into the inflatable member.

32. A system as recited in claim 31, wherein said fluid comprises a gas.

33. A system as recited in claim 31, wherein said fluid comprises a mixture of a gas and a liquid.

34. A system as recited in claim 31, wherein said fluid comprises air, water, oil, perfluorocarbons, diagnostic imaging contrast agent, or saline solution.

35. A system as recited in claim 31, wherein said fluid comprises a liquid.

36. A system as recited in claim 24, wherein said elongate shaft comprises stainless steel hypodermic tubing, polyimide, polyethylene, polystyrene, polycarbonate, extrudable polymer, thermoplastic, silicone, rubber, composite, brass, titanium, aluminum, or ceramic.

37. A system according to claim 24, wherein said tip of said shaft is pointed to allow direct insertion of the tip and shaft into body tissue.

38. A system as recited in claim 24:
wherein said elongate shaft is dimensioned to be coupled with a catheter placement device having a slightly larger diameter than said shaft;
wherein said catheter placement device is placed over the tip and distal end of said shaft and inflatable member during insertion and placement; and wherein said catheter placement device is configured to decouple from said shaft after insertion and placement of the shaft into the body.

39. A system as recited in claim 24:
wherein said elongate shaft and said inflatable member is placed within a catheter placement device having a slightly larger diameter than said shaft and is placed over the distal portion;
wherein said catheter placement device is placed over the tip and distal end of said shaft and inflatable member during insertion and placement; and
wherein said catheter placement device is configured to slide back on said shaft after insertion and placement of the shaft into the body.

40. A system as recited in claim 24, wherein said inflatable member is made of an elastic material that is configured to expand during inflation.

41. A system as recited in claim 40, wherein said inflatable member is configured to take a shape when inflated at the location that is adapted to either correspond to a shape along at least one of the adjacent tissue, the target tissue, or a space at the location between the adjacent tissue and the target tissue, or to displace one of the adjacent tissue or target tissue to a predetermined position relative to the other.

42. A system asd recited in claim 24, wherein said inflatable member is made of an inelastic material that is configured to inflate to a predetermined volume and shape.

43. A system as recited in claim 42, wherein said predetermined shape is configured to either substantially correspond with a shape along at least one of the adjacent tissue, the target tissue, or a space at the location between the adjacent tissue and the target tissue, or to displace one of the adjacent or target tissue to a predetermined position relative to the other.

44. A system as recited in claim 24, wherein said inflatable member is made at least in part of a porous material that is configured to allow the transfer of fluid from the interior of said inflatable member to the exterior of said inflatable member.

45. A system as recited in claim 24, wherein said inflatable member has a metallized surface that is capable of conducting an electric current.

46. A system as recited in claim 24, wherein said inflatable member is optically transparent.

47. A system as recited in claim 24, wherein said inflatable member is optically opaque.

48. A system as recited in claim 24, wherein said inflatable member has a generally spherical shape when inflated.

49. A system as recited in claim 24, wherein said inflatable member has a generally ovoid shape when inflated.

50. A system as recited in claim 24, wherein said inflatable member has a generally spoon shape when inflated.

51. A system as recited in claim 24, wherein said inflatable member has a generally elliptical shape when inflated.

52. An apparatus as recited in claim 24, wherein said inflatable member has a generally cylindrical shape when inflated.

53. A system as recited in claim 24:
wherein said inflatable member includes a plurality of chambers; and
each of said chambers is in fluid communication with at least one other chamber.

54. A system as recited in claim 24, wherein said inflatable member further comprises:
a plurality of partitions compartmentalizing the interior of said inflatable member; and
each compartment is configured to inflate independently of the other compartments.

55. A system as recited in claim 24, wherein said inflatable member is made from a material comprising silastic, silicone, c-flex, polyester, Mylar, polyurethane, polyethylene, polyvinyl, latex, or rubber.

56. A system as recited in claim 24, wherein:
the energy source comprises a radiation source adapted to deliver a therapeutic amount of radiation energy to the target tissue; and
the inflatable member when inflated at least in part with the material at the location comprises a substantial radiation shield that is adapted to substantially isolate the adjacent tissue from the therapeutic amount radiation energy delivered into the target tissue from the radiation source.

57. A system as recited in claim 24, wherein:
said energy source comprises an ultrasound energy source configured to deliver a therapeutic amount of ultrasound energy to the target tissue; and
said material is characterized as having an acoustic impedance such that the inflatable member when inflated at least in part with the material comprises an ultrasound energy shield that is adapted to substantially isolate the adjacent tissue from the therapeutic amount of ultrasound energy delivered into the target tissue from the ultrasound energy source.

* * * * *

UNITED STATES PATENT AND TRADEMARK OFFICE
CERTIFICATE OF CORRECTION

PATENT NO. : 6,746,465 B2 Page 1 of 1
DATED : June 8, 2004
INVENTOR(S) : Chris J. Diederich and Dana L. Deardorff It is certified that error appears in the above-identified patent and that said Letters Patent is hereby corrected as shown below:

<u>Title page,</u>
Item [73], Assignee, after "The Regents of the University of California, Oakland CA (US)", add the following -- Acoustic Medsystems, Inc., Champaign IL (US) --.

Signed and Sealed this

Twenty-fifth Day of October, 2005

JON W. DUDAS
*Director of the United States Patent and Trademark Office*